(12) United States Patent
Zhao

(10) Patent No.: US 11,572,664 B2
(45) Date of Patent: Feb. 7, 2023

(54) ASPHALT DENSITY ESTIMATION SYSTEM, AND RELATED METHOD OF REDUCING SIGNAL NOISE

(71) Applicants: VOLVO CONSTRUCTION EQUIPMENT AB, Eskilstuna (SE); Yaang Zhao, Mechanicsburg, PA (US)

(72) Inventor: Yaang Zhao, Mechanicsburg, PA (US)

(73) Assignee: VOLVO CONSTRUCTION EQUIPMENT AB, Eskilstuna (SE)

(*) Notice: Subject to any disclaimer, the term of this patent is extended or adjusted under 35 U.S.C. 154(b) by 106 days.

(21) Appl. No.: 16/977,932

(22) PCT Filed: Mar. 21, 2018

(86) PCT No.: PCT/US2018/023456
§ 371 (c)(1),
(2) Date: Sep. 3, 2020

(87) PCT Pub. No.: WO2019/182575
PCT Pub. Date: Sep. 26, 2019

(65) Prior Publication Data
US 2021/0363706 A1 Nov. 25, 2021

(51) Int. Cl.
*E01C 23/01* (2006.01)
*G01N 9/24* (2006.01)
(Continued)

(52) U.S. Cl.
CPC .............. *E01C 23/01* (2013.01); *G01N 9/24* (2013.01); *G01N 29/12* (2013.01); *G01N 29/42* (2013.01)

(58) Field of Classification Search
CPC .......... E01C 23/01; G01N 9/24; G01N 29/12; G01N 29/42
See application file for complete search history.

(56) References Cited

U.S. PATENT DOCUMENTS

| 4,422,333 A | * | 12/1983 | Leon | ..................... G01H 1/006 73/660 |
| 5,614,670 A | | 3/1997 | Nazarian et al. | |

(Continued)

FOREIGN PATENT DOCUMENTS

| CN | 101691731 A | 4/2010 |
| CN | 102203582 A | 9/2011 |

(Continued)

OTHER PUBLICATIONS

China Office Action dated Nov. 1, 2021 in corresponding China Patent Application No. 201880091394.2, 10 pages.

(Continued)

*Primary Examiner* — Natalie Huls
*Assistant Examiner* — Cynthia L Davis
(74) *Attorney, Agent, or Firm* — Venable LLP; Jeffri A. Kaminski

(57) ABSTRACT

An asphalt density estimation system includes a measurement device configured to output a measurement signal; a time synchronization unit configured to sample the measurement signal to obtain a sampled measurement signal and identify periodic sampling points of the sampled measurement signal across a plurality of periods. The system also includes a time synchronous averaging unit configured to construct a modified measurement signal in the time domain by: for at least one sampling point within the period, averaging a plurality of the periodic sampling points across periods to obtain an average periodic data point for the at least one sampling point, and constructing the modified measurement signal using the average periodic data point for the at least one sampling point. The system further includes a density calculation unit configured to determine asphalt density values based on the modified measurement signal;

(Continued)

and a display unit configured to display the determined asphalt density values.

11 Claims, 8 Drawing Sheets

(51) Int. Cl.
*G01N 29/12* (2006.01)
*G01N 29/42* (2006.01)

(56) References Cited

U.S. PATENT DOCUMENTS

| | | | | |
|---|---|---|---|---|
| 5,621,656 | A | * | 4/1997 | Langley ............... F16F 7/1005 73/648 |
| 2006/0096354 | A1 | | 5/2006 | Commuri et al. |
| 2010/0172696 | A1 | | 7/2010 | Commuri |
| 2011/0293369 | A9 | | 12/2011 | Commuri |
| 2015/0030392 | A1 | | 1/2015 | Commuri et al. |

FOREIGN PATENT DOCUMENTS

| | | |
|---|---|---|
| CN | 103344702 A | 10/2013 |
| CN | 106940370 A | 7/2017 |

OTHER PUBLICATIONS

Bjorklund, N et al; Real-time Sampling of Ground Penetrating Radar and Related Processing; Lulea University of Technology; Jan. 17, 2005; 2005:039 CIV-ISSN:1402-1617—ISRN: LTU-EX-05/039-SE; [retrieved on Apr. 30, 2018]. Retrieved from the Internet <URL: http://www.diva-portal.org/smash/get/diva2:1026648/FULLTEXT01.pdf>; abstract; pp. 5-13, 15-16.

Shangguan, P; Developmentof Algorithms for Asphalt Pavement Compaction Monitoring Utilizing Ground Penetrating Radar; University of Illinois at Urbana-Champaign, 2014; [retrieved on Apr. 30, 2018], Retrieved from the Internet <URL: https://www.ideals.illinois.edu/bitstream/handle/2142/73067/Pengcheng_Shangguan.pdf?sequence=1>; abstract; p. 24.

Hussain, ZM et al; Digital Signal Processing; Chapter 2: Discrete and Digital Signals and Systems; Springer-Verlag Berlin Heidelberg; 2011; DOI: 10.1007/978-3-642-15591-8_2; p. 63, paragraphs 1-3; p. 97, figure 2.21, p. 98, figure 2.23.

Bjurstrom, H; Non-contact Surface Wave Measurements on Pavements; Doctoral Thesis; KTH Royal Institute of Technology; Nov. 11, 2016 [retrieved on Apr. 30, 2018], Retrieved from the Internet <URL: https://www.diva-portal.org/smash/get/diva2:1073021/FULLTEXT01.pdf>; abstract; pp. 2, 24, 30.

Heisey, JS et al; Moduli of Pavement Systems from Spectral Analysis of Surface Waves; Transportation Research Record 852 ; pp. 22-31; 1982 [retrieved on Apr. 30, 2018]. Retrieved from the Internet: <URL: http://onlinepubs.trb.org/Onlinepubs/trr/1982/852/852-004.pdf); entire document.

International Search Report and Written Opinion dated May 31, 2018 in corresponding PCT Application No. PCT/US2018/023456, 11 pages.

Chinese Office Action dated May 31, 2022 in corresponding Chinese Patent Application No. 201880091394.2, 18 pages.

* cited by examiner

ASPHALT DENSITY ESTIMATION SYSTEM, AND RELATED METHOD OF REDUCING SIGNAL NOISE

CROSS-REFERENCE TO RELATED APPLICATIONS

This application is a U.S. National Stage application of PCT/US2018/023456, filed Mar. 21, 2018, and published on Sep. 26, 2019, as WO 2019/182575 A1, all of which is hereby incorporated by reference in its entirety.

BACKGROUND

1. Technical Field

The present disclosure relates to signal processing, and more specifically to signal processing in an asphalt density estimation system, and related method of reducing signal noise.

2. Introduction

An asphalt density estimation system in a compactor is capable of estimating the level of compaction of asphalt or other road materials during its construction. The response of the compactor's vibratory roller is determined by the frequency of its vibratory motors and the natural vibratory modes of the compactor. The asphalt density estimation system can estimate the compacted density of the pavement based on the response of the vibratory roller. However, the measured response of the vibratory roller is subjected to noises, for example, introduced by the instruments used for measuring vibration of the roller drum. Without treatment, the noise in the raw signal can affect the results of digital signal processing (e.g., Fast Fourier Transform). This can ultimately affect the accuracy of the density estimates of the asphalt. Since the value of the density is correlated with signal power changes within a small range of about 5% (approximately 89% to 94% density in typical road construction applications), reducing the impact of noise becomes important for the asphalt density estimation system.

U.S. Patent Application Publication No. 2015/0030392 A1 to Commuri et al. ("Commuri") discloses an apparatus for the compaction of roadway materials that includes a compaction analyzer for calculating stiffness during construction of the roadway. Commuri further discloses a feature extractor module 34 that implements a Fast Fourier Transform to efficiently extract the different frequency components of the responsive vibratory signals of a roller 10. However, Commuri does not disclose the use of signal noise reductions, for example, in a time domain.

SUMMARY

According to a first aspect of the invention, an asphalt density estimation system includes a measurement device configured to output a measurement signal; a time synchronization unit configured to: sample the measurement signal to obtain a sampled measurement signal, identify a period in the time domain for the sampled measurement signal, identify a number of sampling points across the period, and identify periodic sampling points of the sampled measurement signal across a plurality of periods based on the identified period. The asphalt density estimation system also includes a time synchronous averaging unit configured to construct a modified measurement signal in the time domain by: for at least one sampling point within the period, averaging a plurality of the periodic sampling points across periods to obtain an average periodic data point for the at least one sampling point, and constructing the modified measurement signal using the average periodic data point for the at least one sampling point. The asphalt density estimation system also includes a density calculation unit configured to determine asphalt density values based on the modified measurement signal; and a display unit configured to display the determined asphalt density values.

According to a second aspect of the invention, a method for reducing signal noise includes receiving, by a processor, a measurement signal in the form of an analog DC electrical signal; sampling, by the processor, the measurement signal to obtain a sampled measurement signal; identifying, by the processor, a period in the time domain for the sampled measurement signal; identifying, by the processor, a number of sampling points across the period; identifying, by the processor, periodic sampling points of the sampled measurement signal across a plurality of periods based on the identified period; for at least one sampling point within the period, averaging by the processor, a plurality of the periodic sampling points across periods to obtain an average periodic data point for the at least one sampling point; and constructing, by the processor, the modified measurement signal using the average periodic data point for the at least one sampling point.

Additional features and advantages of the disclosure will be set forth in the description which follows, and in part will be apparent from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

BRIEF DESCRIPTION OF THE DRAWINGS

With reference to the appended drawings, below follows a more detailed description of example embodiments of the invention.

DETAILED DESCRIPTION

A system, method, and computer-readable media are disclosed which can be used to estimate asphalt compaction densities for a road surface, such as an asphalt pavement, based on a time synchronous averaging technique for reducing signal noise.

Various embodiments of the disclosure are described in detail below. While specific implementations are described, it should be understood that this is done for illustration purposes only. Other components and configurations can be used without departing from the spirit and scope of the disclosure.

Figure 1:
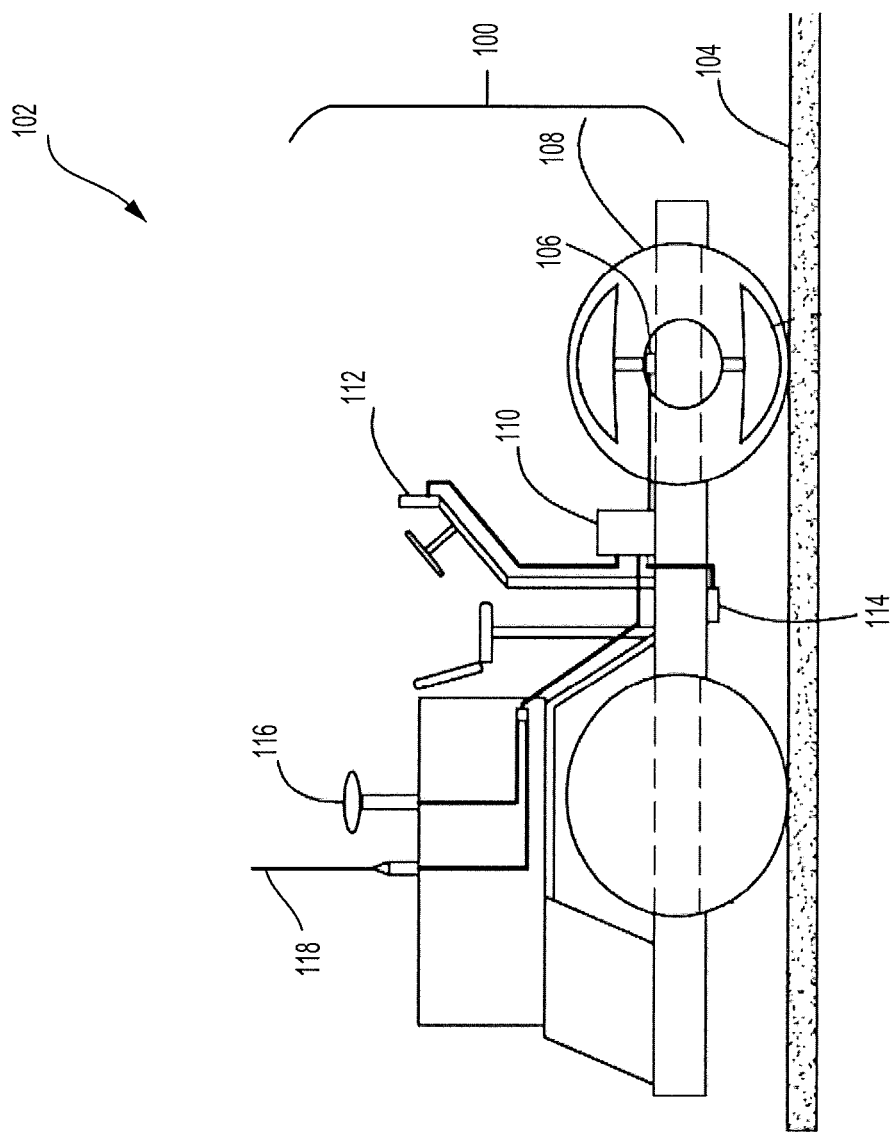
FIG. 1 illustrates an example compactor incorporating an asphalt density estimation system according to an embodiment.

FIG. 1 illustrates an example compactor incorporating an asphalt density estimation system 100 according to an embodiment. The compactor 102 can drive over a road surface, such as an asphalt pavement 104. Together, the compactor 102 and the asphalt pavement 104 can form a coupled system. The asphalt density estimation system 100 can estimate the density of the asphalt pavement 104 continuously in real time, during its construction.

As shown in FIG. 1, the compactor 102 includes a compactor drum 108 (e.g., having eccentric weights) that rolls over and compacts the asphalt pavement 104. The asphalt density estimation system 100 can include one or more measurement devices, such as an accelerometer 106, mounted to or otherwise associated with the compactor drum 108 for measuring the vibrations of the drum 108 during operation. The asphalt density estimation system 100 can include an asphalt compaction analyzer 110 that receives measurement data or signal from the accelerometer 106, e.g., in the form of an analog DC signal, to estimate the density of the asphalt pavement 104 based on the received signal. The received raw signal can be pre-processed via a signal processing unit for reducing noise in the raw signal, for example, in a time domain of the raw signal, as will be described in detail below. The signal processing unit can be included in the asphalt compaction analyzer 110. The asphalt compaction analyzer 110 can comprise a computing device having one or more processors, as described in more detail herein.

The asphalt compaction analyzer 110 can include a density calculation unit that calculates asphalt density based on the signal received from the accelerometer 106, as described in more detail below.

The asphalt density estimation system 100 can further include a display 112 for displaying density output from the asphalt density analyzer 110. The density output can be illustrated on the display 112 as a density map corresponding to the asphalt pavement 104. The density output can be viewed and relied upon by an operator of the compactor 102 for the measure of compaction of the asphalt pavement 104. The density output can be continuously and dynamically updated based on the conditions of the asphalt pavement 104.

The asphalt density estimation system 100 can further include one or more temperature sensors 114 for measuring the surface temperature of the asphalt pavement 104. A global positioning system (GPS) 116 can also be included in the asphalt density estimation system 100. The GPS can be used to provide locations of the compactor 100 as it moves and can be coordinated with the asphalt density analyzer 110, such that the location of the densities on the pavement 104 can be mapped against the GPS coordinates. The asphalt density estimation system 100 can further include a rover radio 118 for calibrating the GPS locations to ensure the GPS location accuracy.

To reduce noise in the raw signal collected from the measurement device associated with the compactor drum 108 (e.g., the accelerometer 106), a time domain noise reduction technique, herein referred to as a time synchronous averaging (TSA) technique, can be used. The TSA technique can be used to reduce or minimize signal noise whose source can be attributed or traced to the time domain. This can include accelerometer 106 noise incurred in measuring the signal. According to an embodiment, the accelerometer output can be an analog DC electrical signal in the range of 0 to 5 volts.

The TSA technique differs from typical recursive and non-recursive filters because it does not use consecutive sample values of the unfiltered signal. Instead, it takes average of sample values that are at the same relative locations on the raw signal waves. For easy understanding, the formulas of the TSA technique are first shown for a specific example signal based on the following assumptions, then formulas for generic periodical signals are presented by using parameters in equations.

In this example, the raw signal can be a sine wave augmented with a random number signal with zero mean and certain standard deviation, the number of sample values used for TSA is 4, the fundamental frequency of the signal is 50 Hz, and the sampling frequency is 1000 Hz. In this case the waveform period is 20 ms (1/50 Hz), represented by 20 samples per period at a rate of one sample per millisecond (20 ms/(1/1000 Hz)). Therefore, there are 20 distinctive (but repetitive) relative location points (with an 18 degree interval between two consecutive points) on a complete wave length of 360 degrees.

The following parameters are defined for a generic periodical signal for processing using TSA:

n: a reference index number for a data point on the signal wave;

n+1: the data point immediately following the reference number;

p: period of the wave, equals 20 in the above example;

k: number of samples used in calculating an average, equals 4 in the above example;

X: raw signal; and

Y: signal after TSA.

For the above assumed specific example signal, the TSA technique formulas are as follows:

$$Y(n + 3*20) = ((X(n) + X(n + 20) + X(n + 2*20) + X(n + 3*20))/4$$

$$Y(n + 1 + 3*20) =$$
$$((X(n + 1) + X(n + 1 + 20) + X(n + 1 + 2*20) + X(n + 1 + 3*20))/4$$

$$Y(n + 2 + 3*20) = ((X(n + 2) + X(n + 2 + 20) +$$
$$X(n + 2 + 2*20) + X(n + 2 + 3*20))/4$$

$$\ldots$$

$$Y(n + 20 - 1 + 3*20) = ((X(n + 20 - 1) + X(n + 20 - 1 + 20) +$$
$$X(n + 20 - 1 + 2*20) + X(n + 20 - 1 + 3*20))/4$$

The TSA technique formulas for a generic periodical signal with the aforementioned defined parameters are as follows:

$$Y(n + (k - 1)*p) = ((X(n) + X(n + p) + \ldots + X(n + (k - 1)*p))/k$$

$$Y(n + 1 + (k - 1)*p) =$$
$$((X(n + 1) + X(n + 1 + p) + \ldots + X(n + 1 + (k - 1)*p))/k$$

$$Y(n + 2 + (k - 1) * p) =$$
$$((X(n + 2) + X(n + 2 + p) + \ldots + X(n + 2 + (k - 1) * p))/k$$
$$\ldots$$
$$Y(n + p - 1 + (k - 1) * p) = ((X(n + p - 1) + X(n + p - 1 + p) +$$
$$\ldots + X(n + p - 1 + (k - 1) * p))/k$$

In the above lines of formulas, the ellipses between terms represent additional terms that fit the same pattern as defined by adjacent terms. The ellipses between lines represent additional equations that fit the same pattern as defined by adjacent equations.

Expressed differently, the modified signal generated by the TSA technique can be represented as:

$$Y(n) = \sum_{i=0}^{k-1} \frac{X(n - ip)}{k}$$

Figure 2:
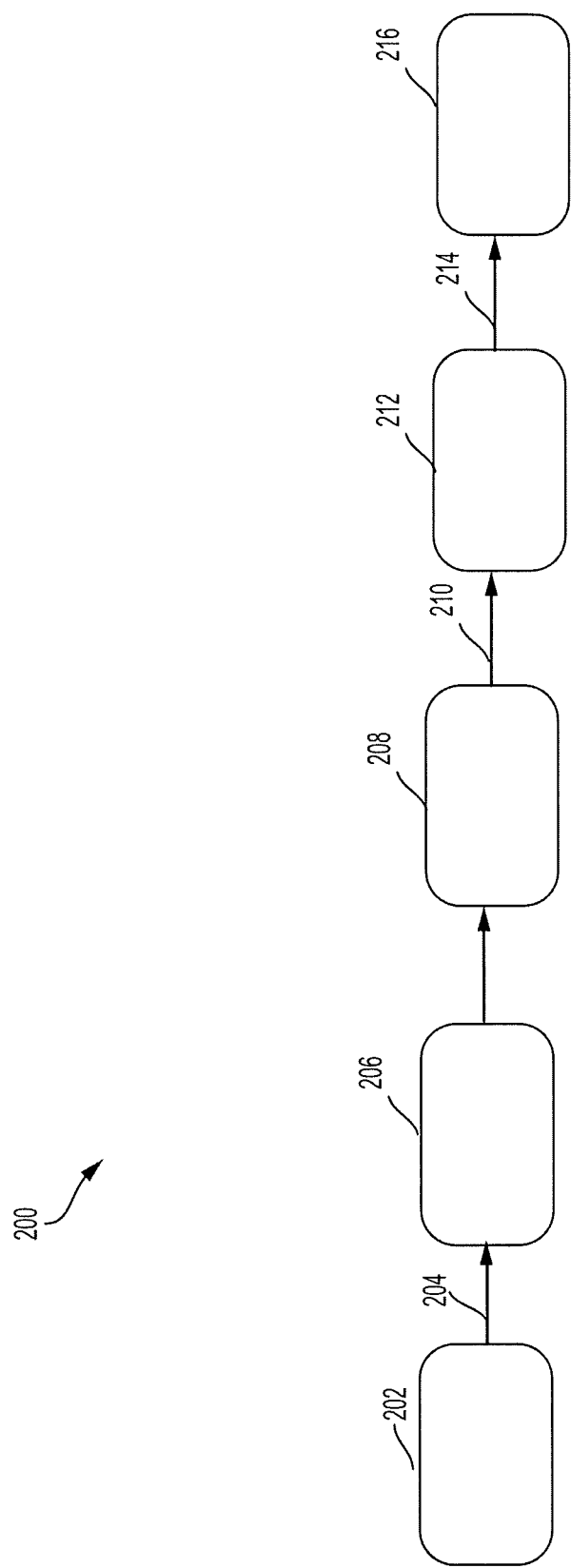
FIG. 2 illustrates an example asphalt density estimation system.

Where:
k: number of periods (number of raw data points used to compute one new data point)
p: period FIG. 2 illustrates an example asphalt density estimation system 200 that can incorporate the TSA technique. The system 200 can include a measurement device 202 configured to output a measurement signal 204. A time synchronization unit 206 can be configured to sample the measurement signal 202 (e.g., at a sampling rate of 4000 Hz) to obtain a sampled measurement signal. The time synchronization unit 206 can also identify a period in the time domain for the sampled measurement signal, and identify a number of sampling points across the period. To determine the period, the sample number differences in every two consecutive peaks/troughs of the sampled measurement signal can be tracked, which can form a vector having those sample number differences as elements or a sequence of those sample number differences. The sequence of sample number differences can be averaged to obtain an averaged sample number difference. The sampling rate can then be divided by the averaged sample number difference to obtain a frequency of the sampled measurement signal. The period can be determined by inversing the frequency.

Additionally, the time synchronization unit 206 can identify periodic sampling points of the sampled measurement signal across a plurality of periods based on the identified period. Specifically, in each of the plurality of periods, each sampling point having a relative same location or phase (e.g., at each 18 degrees of a period) are identified as the periodic sampling points at that relative same location or phase across the plurality of periods.

Still referring to FIG. 2, the system 200 can also include a time synchronous averaging unit 208 configured to construct a modified measurement signal 210 in the time domain based on the sampled measurement signal 204. For example, for at least one sampling point within the period, the time synchronous averaging unit 208 can average a plurality of the periodic sampling points across periods to obtain an average periodic data point for the at least one sampling point. The time synchronous averaging unit 208 averages periodic sampling points for a plurality of sampling points within each period, to obtain multiple average periodic data points within each period. The time synchronous averaging unit 208 can construct the modified measurement signal using the average periodic data point(s) for the at least one sampling point. For example, at each sampling location in each period, an average periodic data point can be obtained. By plotting those periodic data points based on the sampling rate, the modified measurement signal can be constructed. The averaging process can gradually eliminate random noise of the raw signal based on the assumption that the random noise is not coherent with the trigger signal. Only the signal that is synchronous and coherent with the trigger signal can persist in the averaged calculation. With the TSA technique, the amount of reduction in signal noise as represented by a standard deviation is inversely proportional to the square root of the number used to calculate the averages of signal values.

The system 200 can further include a density calculation unit 212 configured to determine asphalt density values 214 based on the modified measurement signal 210. The system 200 can also include a display unit configured to display the determined asphalt density values 216. For example, the density calculation unit 212 can use a digital signal processing technique (e.g., Fast Fourier Transform) to extract the vibration signature or characteristics from the modified measurement signal. Additionally, a neural network (NN) classifier can associate the vibration characteristics to the density of the asphalt pavement, as disclosed by U.S. Patent Application Publication No. 2015/0030392 A1 to Commuri et al., the entire contents of which are incorporated herein by reference. Other techniques for calculating density of the asphalt based on the vibration characteristics can be found in U.S. Pat. No. 8,190,338 to Commuri, U.S. Pat. No. 5,952,561 to Jaselskis, and U.S. Patent Application Publication No. 2006/0096354 to Commuri. Additional techniques for calculating density of the asphalt based on the vibration characteristics can be found in Minchin et al., "Computer Applications in Intelligent Compaction," Journal of Computing in Civil Engineering, Vol. 22, No. 4, July/August 2008.

The measurement device 202 can be an accelerometer 106 (see FIG. 1), and accordingly, the measurement signal 204 can be a signal reflecting vibration of the drum 108 (see FIG. 1).

The time synchronization unit 206 can be any suitable signal processing unit that can include one or more processors, memory, and/or any other hardware. The unit 206 can be used to generate an internal trigger signal and synchronize the measurement signal 204 using the internal trigger signal. According to an embodiment, the time synchronization unit 206 can use the trigger signal to identify the periodic sampling points of the sampled measurement signal across the plurality of periods. The trigger signal can have a period or frequency value that is based on the fundamental frequency of the measurement signal. For example, the trigger signal can have a frequency that is equal to the fundamental frequency of the raw signal (e.g., the measurement signal) received from the accelerometer 106.

The design and identification of an internal trigger signal can have the following considerations, features, and/or advantages:

(1) The trigger signal eliminates the use of a Fast Fourier Transform result to determine signal fundamental frequency or period. Instead, it uses raw vibration data from time domain to do so.

(2) The trigger signal identifies peaks or troughs in the "sine wave" like signal by detecting a local maximum or minimum.

(3) Double counting of peaks can be avoided if one sample value near the peak is less than the previous sample value and the subsequent sample value.

(4) Double counting of peaks or no counting of peaks can be avoided in case of a flat peak where two consecutive samples have the same values which are local maximums.

(5) The trigger signal keeps track of the sample number difference in every two consecutive peaks (e.g., 19, 20, 20, and 19).

(6) The trigger signal takes the average of the sequence or vector of the sample number differences, which result in the average period (peak to peak) of the "sine" wave.

(7) The average fundamental frequency of the raw signal equals 1000 divided by the average period.

(8) Other features may be added for robustness to ensure that all the peak to peak sample number differences are close to their mean or median value.

(9) In the event that the minimum or the maximum of the sequence of the sample number differences differ significantly from the mean, the median instead of the mean of the sequence may be used to calculate the average period.

The trigger signal can be continuously updated. In some circumstances, the operational vibration frequency of the drum 108 can be changed due to, for example, different pavement materials. In other circumstances, the operator of the compactor 102 can switch to a different operational frequency. In such cases, the fundamental frequency of the measurement signal can change accordingly. To synchronize the measurement signal of different fundamental frequency, the trigger signal can be updated accordingly.

The time synchronous averaging unit 208 can be any suitable signal processing unit that can include one or more processors, memory, and/or any other hardware. The unit 208 can be used to carry out the TSA technique to generate the modified signal 210 with reduced noise from the measurement signal 204, as described above.

The density calculation unit 212 can be any suitable device that can include one or more processors, memory, and/or any other hardware. The asphalt density values 214 can be determined based on the modified measurement signal 210, by any suitable method, for example, the methods described above.

Figure 3:
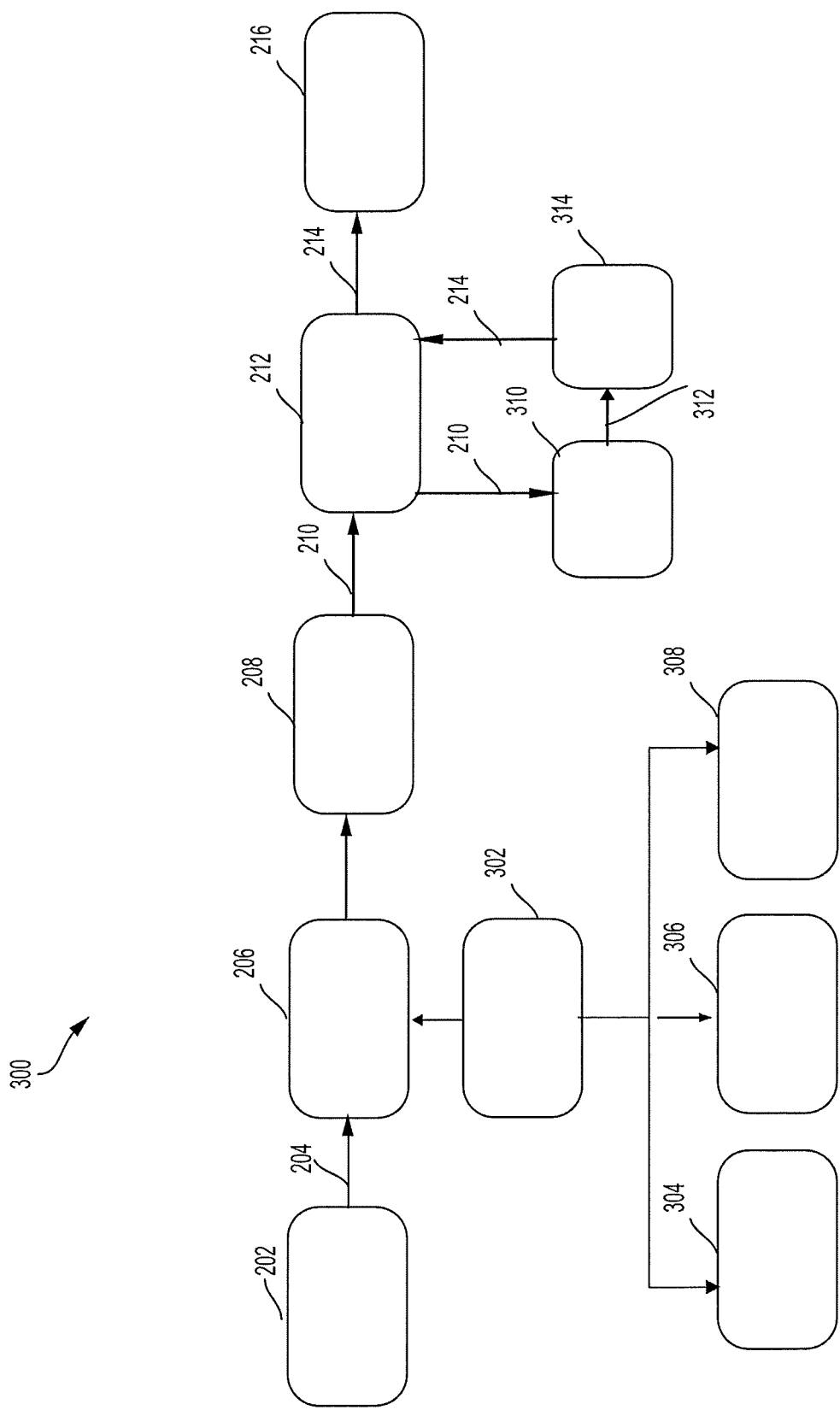
FIG. 3 illustrates another example asphalt density estimation system.

FIG. 3 illustrates another example asphalt density estimation system 300. The time synchronization unit 206 can further include a trigger signal generator 302 for generating a trigger signal to synchronize the measurement signal 204. The trigger signal generator 302 can be any suitable device that can include one or more processors, memory, and/or any other hardware.

The trigger signal can be an internal trigger signal. For example, the internal trigger signal can be generated by: identifying peaks or troughs of the sampled measurement signal by determining local maxima or minima, respectively; calculating an average number of sampling points between consecutive peaks or consecutive troughs; rounding the average number of the sampling points to a positive integer number; and using the positive integer number as the trigger signal. The generation of the internal trigger signal may further comprise dividing the calculated average number of sampling points between consecutive peaks or consecutive troughs by the sampling rate of the sampled measurement signal to obtain a frequency value of the trigger signal. For example, the sample number differences in every two consecutive peaks/troughs of the sampled measurement signal can be tracked, which can form a vector having those sample number differences as elements or a sequence of those sample number differences. The sequence of sample number differences can be averaged to obtain an averaged sample number difference. This averaged value can be rounded to a positive integer number which can be used as an internal trigger for the TSA technique. The sampling rate can then be divided by the averaged sample number difference to obtain a frequency of the sampled measurement signal. The period can be determined by inversing the frequency.

The system 300 can further include a signal processing unit 310. The unit 310 can be configured to receive the modified measurement signal 210 and transform the modified measurement signal 210 from a time domain signal to a frequency domain signal, via, for example, a Fast Fourier Transform technique.

The frequency domain signal 312 can be input into a neutral network classifier 314 to generate the asphalt density values 214 from the frequency domain signal 312, as described above in connection with the density calculation unit 212 of FIG. 2.

Figure 4:
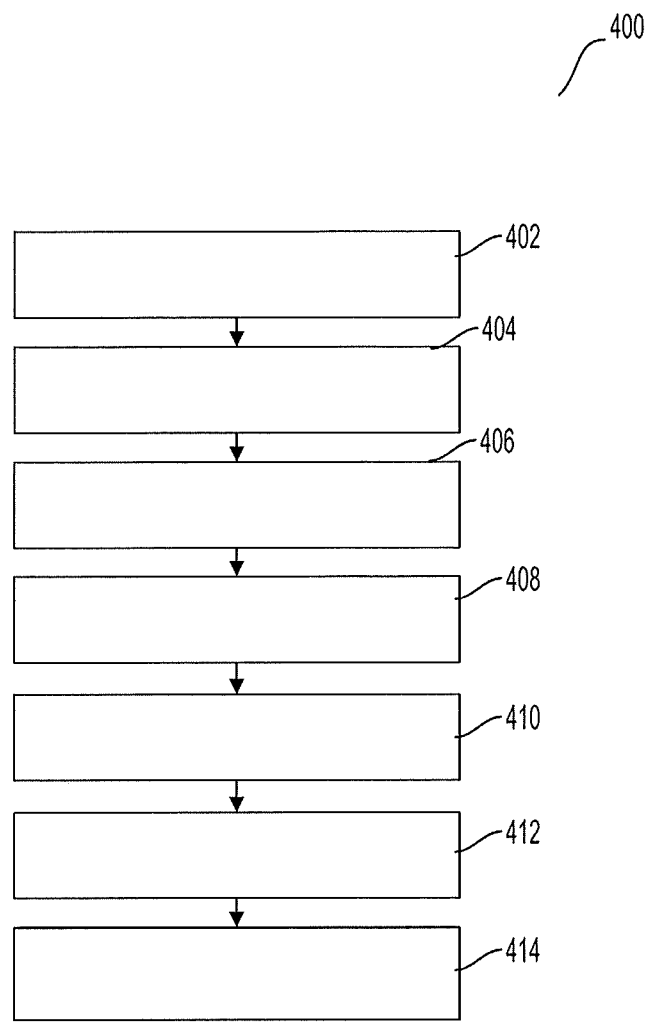
FIG. 4 illustrates an example process for reducing signal noise.

FIG. 4 illustrates an example method 400 for reducing signal noise, according to an example embodiment. The method 400 can be implemented in the systems 100, 200, and/or 300, and can include the following steps.

At step 402, a measurement signal in the form of an analog DC electrical signal can be received by a processor. For example, the measurement signal can be the signal 204 generated by the measurement unit 202, and the processor can be one or more of the processors disclosed herein.

At step 404, the measurement signal can be sampled to obtain a sampled measurement signal.

At step 406, a period in the time domain for the sampled measurement signal can be identified.

At step 408, a number of sampling points across the period can be identified.

At step 410, periodic sampling points of the sampled measurement signal across a plurality of periods can be identified based on the identified period.

At step 412, for at least one sampling point within the period, a plurality of the periodic sampling points across periods are averaged, to obtain an average periodic data point for the at least one sampling point. According to embodiments, average periodic data points can be calculated for multiple sampling points within each period.

At step 414, the modified measurement signal can be constructed using the average periodic data point(s) for the at least one sampling point.

The method 400 can further include identifying periodic sampling points of the sampled measurement signal across the plurality of periods using a trigger signal. The trigger signal can have a period or frequency value that is based on the fundamental frequency of the measurement signal.

Figure 5:
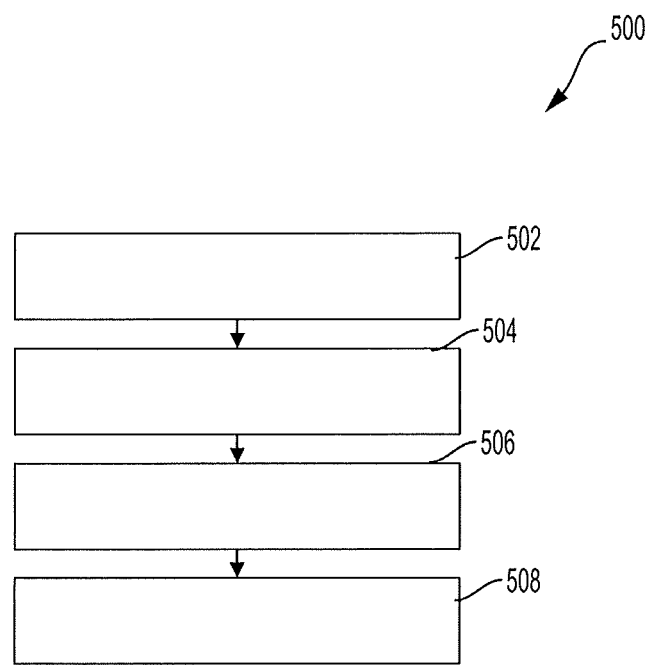
FIG. 5 illustrates an example process for generating a trigger signal.

FIG. 5 illustrates an example process 500 for generating a trigger signal. The method 500 can be implemented by one or more of the processors described herein, and can include the following steps.

At step 502, peaks or troughs of the sampled measurement signal can be identified, by determining local maxima or minima in the raw signal, respectively.

At step 504, an average number of sampling points between consecutive peaks or consecutive troughs can be calculated. For example, the sample number differences in every two consecutive peaks/troughs of the sampled measurement signal can be tracked, which can form a vector having those sample number differences as elements or a sequence of those sample number differences. The sequence of sample number differences can be averaged to obtain an averaged sample number difference (e.g., the average number of sampling points between consecutive peaks or troughs).

At step 506, the calculated average number of sampling points between consecutive peaks or consecutive troughs can be divided using the sampling rate of the sampled measurement signal to obtain a frequency value of the trigger signal.

At step 508, the trigger signal can be continuously updated, for example, in response to changes in the fundamental frequency of the measurement signal. To synchronize the measurement signal of different fundamental frequencies, the trigger signal can be updated accordingly.

Figure 6:
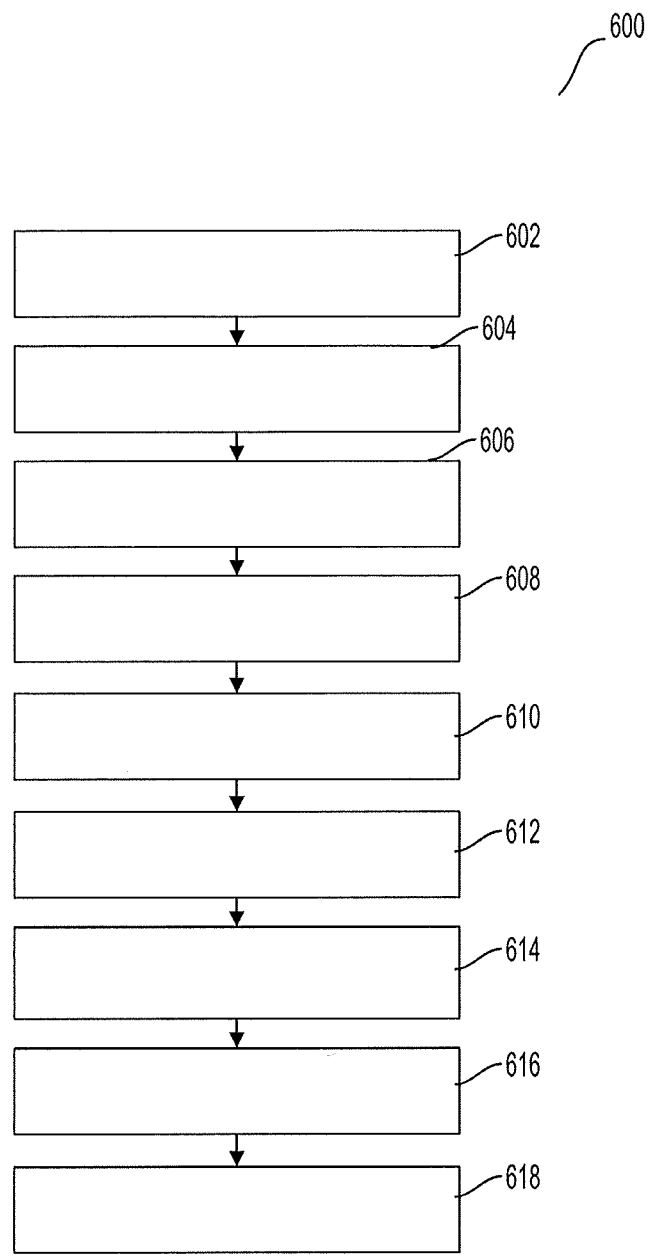
FIG. 6 illustrates an example process for estimating asphalt density.

FIG. 6 illustrates an example process 600 for estimating asphalt density. The method 600 can be implemented on one or more of the processors described herein, and can include the following steps. Steps 602 to 614 are similar or the same as the steps 402 to 414, respectively, of the method 400, so details of steps 602 to 614 previously described are not repeated herein.

At step 602, a measurement signal from a compactor drum in the form of an analog DC electrical signal can be received. For example, the measurement signal can be an analog DC signal output by an accelerometer associated with the compactor drum.

At step 604, the measurement signal can be sampled to obtain a sampled measurement signal.

At step 606, a period in the time domain for the sampled measurement signal can be identified.

At step 608, a number of sampling points across the period can be identified.

At step 610, periodic sampling points of the sampled measurement signal across a plurality of periods can be identified based on the identified period.

At step 612, for at least one sampling point within the period, a plurality of the periodic sampling points across periods are averaged to obtain an average periodic data point for the at least one sampling point.

At step 614, the modified measurement signal can be constructed using the average periodic data point for the at least one sampling point.

At step 616, the modified measurement signal can be transformed to asphalt density values. The step 616 can further include transforming the modified measurement signal from a time-domain signal into a frequency-domain signal, and correlating the frequency-domain signal to the asphalt density values. For example, the density values can be obtained using the techniques described above in connection with the density calculation unit 212 of FIG. 2.

At step 618, the asphalt density values can be output, for example, by being displayed on the unit 216.

Figure 7:
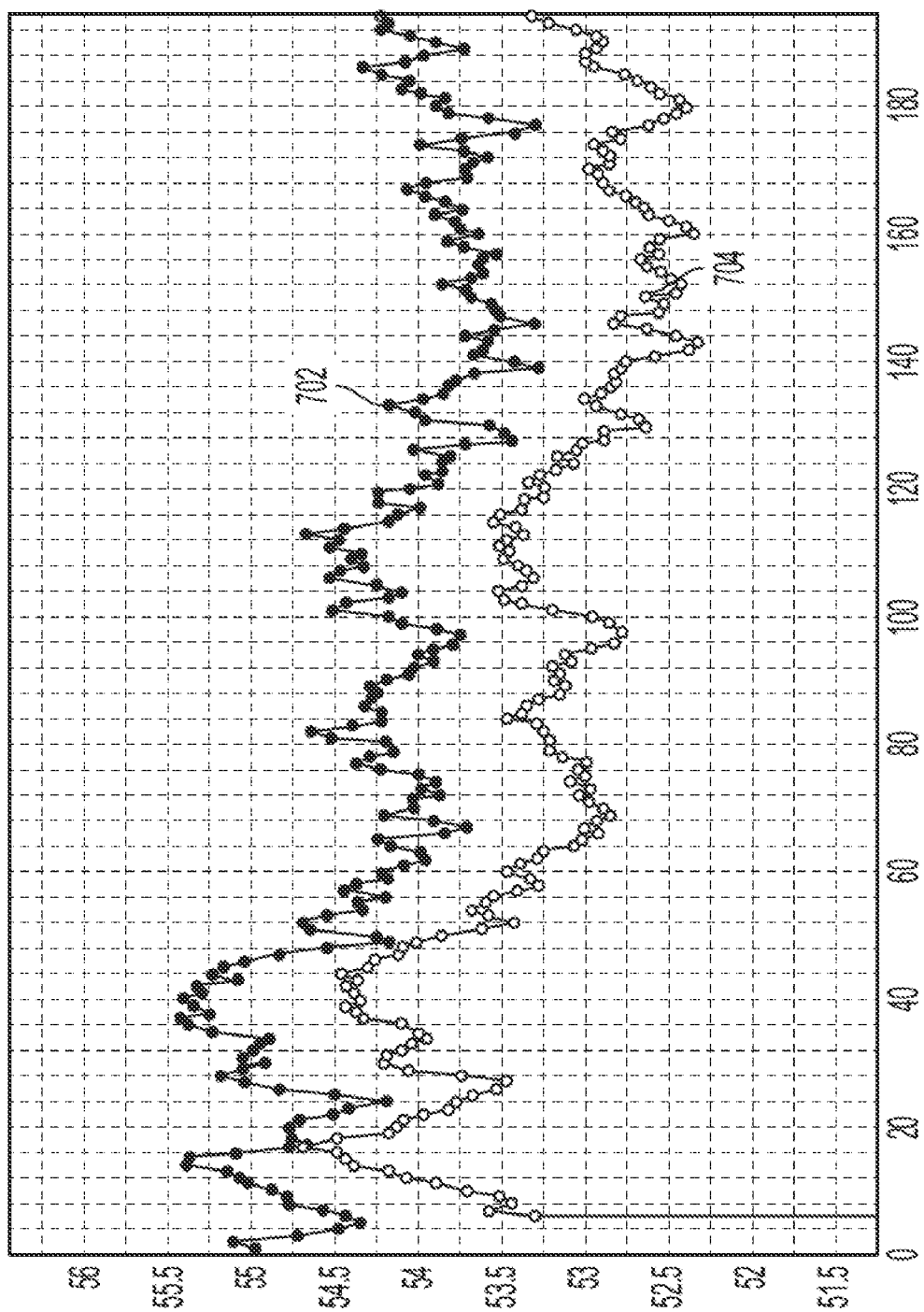
FIG. 7 illustrates a comparison between the power (a frequency domain signal) of a raw signal without reducing signal noise in the time domain and the power of a signal after reducing signal noise of the raw signal in the time domain.

FIG. 7 illustrates a comparison between the power (a frequency domain signal derived from the time domain signal) of a raw signal without reducing signal noise and the power of a signal after reducing signal noise using the TSA technique. Specifically, FIG. 7 compares the power value 704 (from a Fast Fourier Transform) of the signal from the TSA technique, with the power value 702 of the signal without TSA pre-processing. The figure is for 100 seconds of test data. As can be seen, the TSA power time trajectory 704 is smoother than its baseline counterpart 702. This is an indication that the random noise (e.g., in measuring vibration using an accelerometer) effect is reduced by the TSA technique. This provides validation of the technical merit of the TSA technique. Because road surface density estimates are strongly correlated with vibration signal power, density estimation accuracy can be improved due to a reduction in signal noise impact.

Figure 8:
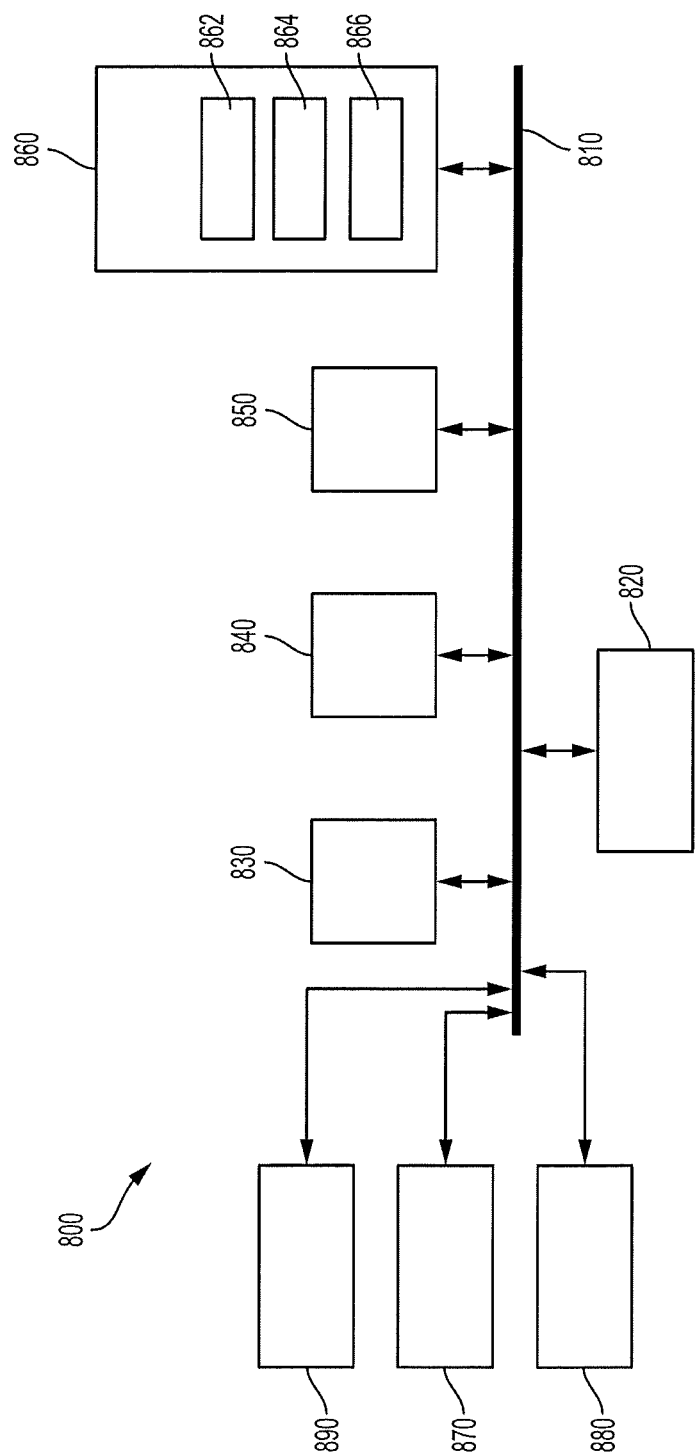
FIG. 8 illustrates an example computer system.

A computer readable medium can be provided for storing instructions for performing the steps of the methods 400, 500 and/or 600 when the program is executed on a computer having one or more processors. FIG. 8 illustrates an example computer system, which can be employed to practice the concepts disclosed herein. However, one of ordinary skill in the art will understand from this disclosure that any number of computer systems, such as a laptop personal computer (PC), tablet PC, or programmable logic controller (PLC) can be used to implement the systems and methods described herein.

With reference to FIG. 8, an exemplary system includes a general-purpose computing device 800, including a processing unit (CPU or processor) 820 and a system bus 880 that couples various system components including the system memory 830 such as read-only memory (ROM) 840 and random access memory (RAM) 850 to the processor 820. The system 800 can include a cache of high-speed memory connected directly with, in close proximity to, or integrated as part of the processor 820. The system 800 copies data from the memory 830 and/or the storage device 860 to the cache for quick access by the processor 820. In this way, the cache can provide a performance boost that avoids processor 820 delays while waiting for data. These and other modules can control or be configured to control the processor 820 to perform various actions. Other system memory 830 can be available for use as well. The memory 830 can include multiple different types of memory with different performance characteristics. It can be appreciated that the disclosure can operate on a computing device 800 with more than one processor 820 or on a group or cluster of computing devices networked together to provide greater processing capability. The processor 820 can include any general purpose processor and a hardware module or software module, such as module 1 862, module 2 864, and module 3 866 stored in storage device 860, configured to control the processor 820 as well as a special-purpose processor where software instructions are incorporated into the actual processor design. The processor 820 can essentially be a completely self-contained computing system, containing multiple cores or processors, a bus, memory controller, cache, etc. A multi-core processor can be symmetric or asymmetric.

The system bus 810 can be any of several types of bus structures including a memory bus or memory controller, a peripheral bus, and a local bus using any of a variety of bus architectures. A basic input/output (BIOS) stored in ROM 840 or the like, can provide the basic routine that helps to transfer information between elements within the computing device 800, such as during start-up.

In one aspect, a hardware module that performs a particular function can include the software component stored in a tangible computer-readable storage medium in connection with the necessary hardware components, such as the processor 820, bus 810, display 870, and so forth, to carry out the function. In another aspect, the system can use a processor and computer-readable storage medium to store instructions which, when executed by the processor, cause the processor to perform a method or other specific actions. The basic components and appropriate variations are contemplated depending on the type of device, such as whether the device 800 is a small, handheld computing device, a desktop computer, or a computer server.

Although the example embodiment described herein employs the hard disk 860, other types of computer-readable media which can store data that are accessible by a computer, such as magnetic cassettes, flash memory cards, digital versatile disks, cartridges, random access memories (RAMs) 850, and read-only memory (ROM) 840, can also be used in the example operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 800, an input device 890 represents any number of input mechanisms, such as a microphone for speech, a touch-sensitive screen for gesture or graphical input, keyboard, mouse, motion input, speech and so forth. An output device 870 can also be one or more of a number of output mechanisms known to those of skill in the art. In some instances, multimodal systems enable a user to provide multiple types of input to communicate with the computing device 800. The communications interface 810 generally governs and manages the user input and system output. There is no restriction on operating on any particular hardware arrangement and therefore the basic features here can easily be substituted for improved hardware or firmware arrangements as they are developed.

The steps outlined in the methods 400, 500, and 600 are exemplary and can be implemented in any combination thereof, including combinations that exclude, add, or modify certain steps.

The various embodiments described above are provided by way of illustration only and should not be construed to limit the scope of the disclosure. Various modifications and changes can be made to the principles described herein without following the example embodiments and applications illustrated and described herein, and without departing from the spirit and scope of the disclosure.

I claim:

1. An asphalt density estimation system comprising:
   a measurement device configured to measure vibrations of a compactor drum and output a measurement signal of the vibrations;
   a time synchronization unit utilizing time synchronous averaging configured to: sample the measurement signal to obtain a sampled measurement signal, identify a period in the time domain for the sampled measurement signal, identify a number of sampling points across the period, and generate a trigger signal and use the trigger signal to identify periodic sampling points of the sampled measurement signal across a plurality of periods based on the identified period, wherein the trigger signal has a period and/or frequency value that is based on the fundamental frequency of the measurement signal;
   a time synchronous averaging unit configured to construct a modified measurement signal in the time domain by: for at least one sampling point within the period, averaging a plurality of the periodic sampling points across the plurality of periods to obtain an average periodic data point for the at least one sampling point, and constructing the modified measurement signal using the average periodic data point for the at least one sampling point;
   a density calculation unit configured to determine asphalt density values based on the modified measurement signal; and
   a display unit configured to display the determined asphalt density values.

2. The asphalt density estimation system of claim 1, wherein the time synchronization unit generates the trigger signal by: identifying peaks or troughs of the sampled measurement signal by determining local maxima or minima, respectively; calculating an average number of sampling points between consecutive peaks or consecutive troughs; rounding the average number of the sampling points to a positive integer number; and using the positive integer number as the trigger signal.

3. The asphalt density estimation system of claim 2, further comprising: dividing positive integer number by the sampling rate of the sampled measurement signal to obtain a frequency value of the trigger signal.

4. The asphalt density estimation system of claim 1, wherein the trigger signal is continuously updated.

5. A compactor, comprising: a compactor drum; and the asphalt density estimation system of claim 1, wherein the measurement device comprises an accelerometer configured to measure vibration of the compactor drum, the accelerometer adapted to output the measurement signal in the form of an analog DC electrical signal.

6. A method for reducing signal noise comprising:
   receiving, from a measurement device, a measurement signal in the form of an analog DC electrical signal which measures vibrations of a compactor drum;
   sampling, by a time synchronization unit utilizing time synchronous averaging, the measurement signal to obtain a sampled measurement signal;
   identifying, by the time synchronization unit, a period in the time domain for the sampled measurement signal;
   identifying, by the time synchronization unit, a number of sampling points across the period;
   generating, by the time synchronization unit, a trigger signal, wherein the trigger signal has a period and/or frequency value that is based on the fundamental frequency of the measurement signal;
   identifying, by the time synchronization unit, periodic sampling points of the sampled measurement signal across a plurality of periods using the trigger signal based on the identified period;
   for at least one sampling point within the period, performing time synchronous averaging by a time synchronous averaging unit of a plurality of the periodic sampling points across the plurality of periods to obtain an average periodic data point for the at least one sampling point; and
   constructing, by the time synchronous averaging unit, a modified measurement signal using the average periodic data point for the at least one sampling point.

7. The method of claim 6, further comprising generating the trigger signal by: identifying, by the time synchronization unit, peaks or troughs of the sampled measurement signal by determining local maxima or minima, respectively; calculating, by the time synchronization unit, an average number of sampling points between consecutive peaks or consecutive troughs; rounding, by the time synchronization unit, the average number of the sampling points to positive integer number; and using the positive integer number as the trigger signal.

8. The method of claim 7, further comprising: dividing, by the time synchronization unit, the positive integer number by the sampling rate of the sampled measurement signal to obtain a frequency value of the trigger signal.

9. The method of claim 6, further comprising: continuously updating the trigger signal using the time synchronization unit.

10. A method for estimating the density of asphalt, comprising: transforming, by a signal processing unit, the modified measurement signal from claim 6 into a frequency-domain signal; correlating, by a density calculation unit, the frequency-domain signal to asphalt density values; and outputting the asphalt density values.

11. A computer readable medium storing instructions for performing the steps of claim 6 when the program is run on a computer having a processor.

\* \* \* \* \*